United States Patent

(12) Lipman et al.

(10) Patent No.: US 6,740,711 B1
(45) Date of Patent: May 25, 2004

(54) HOT MELT PRESSURE SENSITIVE ADHESIVES

(75) Inventors: Roger David Arnold Lipman, Turnhout Bus 2 (BE); Kristine Dhaeze, Gierle (BE)

(73) Assignee: Avery Dennison Corporation, Pasadena, CA (US)

( * ) Notice: Subject to any disclaimer, the term of this patent is extended or adjusted under 35 U.S.C. 154(b) by 0 days.

(21) Appl. No.: 10/110,644

(22) PCT Filed: Oct. 13, 2000

(86) PCT No.: PCT/GB00/03919

§ 371 (c)(1),
(2), (4) Date: Sep. 3, 2002

(87) PCT Pub. No.: WO01/26700

PCT Pub. Date: Apr. 19, 2001

(30) Foreign Application Priority Data

Oct. 14, 1999 (GB) ............................................. 9924374
Oct. 14, 1999 (GB) ............................................. 9924375

(51) Int. Cl.[7] ................................................. C08L 9/00
(52) U.S. Cl. ........................... 525/216; 525/88; 525/98; 525/100; 525/123; 525/191; 525/222; 525/241
(58) Field of Search .............................. 525/88, 98, 100, 525/123, 191, 216, 222, 241, 105

(56) References Cited

U.S. PATENT DOCUMENTS

| | | | | |
|---|---|---|---|---|
| 4,288,358 A | * | 9/1981 | Trotter et al. ............... | 524/474 |
| 4,622,357 A | * | 11/1986 | Tsuchida et al. ............ | 524/270 |
| 4,647,613 A | | 3/1987 | Jadamus et al. | |
| 4,764,535 A | * | 8/1988 | Leicht ......................... | 521/51 |
| 5,559,165 A | | 9/1996 | Paul | |
| 5,859,114 A | | 1/1999 | Davis et al. | |
| 5,891,957 A | | 4/1999 | Hansen et al. | |

FOREIGN PATENT DOCUMENTS

| | | | |
|---|---|---|---|
| DE | 36 18 941 A1 | 12/1987 | |
| JP | 1170678 A | 7/1989 | |
| JP | 2142878 A | 5/1990 | |
| JP | 04045924 A * | 2/1992 | ........... B32B/15/08 |

OTHER PUBLICATIONS

International Search Report of PCT/GB00/03919, dated Mar. 9, 2001.

International Preliminary Examination Report of PCT/GB00/03919, dated Dec. 12, 2001.

* cited by examiner

*Primary Examiner*—Margaret G. Moore
*Assistant Examiner*—Marc S Zimmer
(74) *Attorney, Agent, or Firm*—Christie, Parker & Hale, LLP

(57) ABSTRACT

A pressure sensitive hot melt adhesive composition suitable for use in a variety of medical products, as well as consumer and industrial products, comprises one or more pressure-sensitive adhesive matrices and at least 0.5 wt. %, based on the total formulation of trans-polyoctenamer. The adhesive composition adheres well to human and other mammalian skin, and can be used for example to secure wound dressings and ostomy appliances.

9 Claims, No Drawings

HOT MELT PRESSURE SENSITIVE ADHESIVES

CROSS-REFERENCE TO RELATED APPLICATION

This application claims priority of International application number PCT/GB00/03939, filed Oct. 13, 200, which in turn claims priority of British application number 9924374.3, filed Oct. 14, 1999, and British application number 9924375.0, filed Oct. 14, 1999.

This invention relates to the use of hot melt pressure sensitive adhesives which adhere well to human and other mammalian skin, and are useful in a variety of medical device products, as well as in industrial and consumer pressure sensitive adhesive products.

The requirements for skin contact pressure sensitive adhesives are stringent. They must adhere well to the skin during a variety of environmental conditions and they must also be removable without leaving any residue on the skin, and without causing significant trauma to the skin. Formulation of such adhesives often involves adding a plasticising additive, such as a tackifier or plasticiser, in order to vary one or other properties of the adhesive such as tack, adhesion cohesive strength etc. Many such additives are of relatively low molecular weight, and as such can contribute negative characteristics to the formulation. In particular, such additives can migrate out of the adhesive, and can adversely affect backing and carrier materials, or can remain on the substrate after removal of the adhesive tape.

Pressure sensitive hot melt adhesives are useful in that they can be processed without the concomitant need to evaporate quantities of solvent or water, and thus have advantages over comparable solution and emulsion pressure sensitive adhesives. With the use of hot melt pressure sensitive adhesives, there are reduced environmental concerns, and reduced costs of dealing with those concerns, because no solvent needs to be recovered or incinerated. As far as emulsion adhesives are concerned, the energy associated with the removal of water, with its high latent heat of evaporation, is saved with the use of hot melt pressure sensitive adhesives. However, it has been found difficult in the past to develop suitable hot melt pressure sensitive adhesives that adhere effectively and safely to human skin, and this has limited the opportunities for cost savings that the hot melt processing promises.

There have been many efforts to develop adhesives that fulfil these criteria. For example U.S. Pat. No. 5,559,165 discloses adhesives for skin use that comprise a high molecular weight block copolymer and 60 to 95 parts of a liquid diluent, for example mineral oil. But the mineral oil inherent in these compositions is capable of migration, to a degree determined in part by the nature of the backing material. Again, U.S. Pat. No. 5,891,957 describes adhesive compositions for skin adhesion and bandage applications comprising a styrene-isoprene-styrene triblock or multiarm copolymer and low-molecular weight styrene-isoprene diblock copolymers having a styrene content of 10–25%. In this case the low molecular weight styrene-isoprene diblock copolymer is functioning as the plasticiser. But the problem with such materials is that, although the compositions are said to provide a pressure sensitive adhesive free of migrating chemicals, they are difficult to process, long times being necessary to incorporate the low molecular weight styrene-isoprene diblock copolymers. This is because of the energy necessary to break down the physical crosslinks in the triblock or multiarm copolymer rubber, due to the association of the glassy styrene residues of each polymer chain.

The present invention consists in a pressure sensitive hot melt adhesive comprising one or more pressure sensitive adhesive matrices and optionally tackifiers and/or plasticisers, characterised in that the adhesive also contains an effective amount of trans-polyoctenamer. The adhesives show reduced migration, tendency, staining tendency, improved compatibility of ingredients and ease of processing and can be used on mammalian skin as components of medical devices, as well as in industrial and consumer products.

The trans-polyoctenamer should constitute at least 0.5 wt. % of the total formulation, preferably at least 2 wt. % and more preferably at least 5 wt. %. The preferred formulations contain 5 to 40 wt. % of this component, more preferably 10 to 30 wt. %.

We have made the surprising discovery that if trans-polyoctenamer, a polymeric rubber, is blended with elastomers that are well-known in the art to provide the basis of pressure sensitive adhesive materials, the resulting formulation behaves as though it is a plasticised formulation. Such formulations perform as pressure sensitive adhesives without the concomitant drawbacks of conventional plasticisers such as migration. Processing of such pressure sensitive adhesive formulations incorporating the trans-polyoctenamer is greatly facilitated.

The benefits of using the trans-polyoctenamer are (a) improved compatibility of different ingredients, (b) improved processibility of the formulation, so that significantly lower blending times and/or lower mixing temperatures are possible so that for example temperature sensitive ingredients can be more readily incorporated and (c) improved adhesion.

Formulations according to the present invention may be based upon any suitable pressure sensitive adhesive material or blend of material. The adhesive matrix may be based on for example polyisobutylene, butyl rubber, polyacrylates, polyurethanes, silicone gum, natural gum rubber, SBR rubber or polyvinyl ether. Thermoplastic elastomers such as styrene-isoprene-styrene block copolymers and styrene-ethylene/propylene-styrene block copolymers may be used, and these may require optional tackifiers and plasticisers. Blends or mixtures of elastomers may be more easily employed, because one of the unique characteristics of trans-polyoctenamer is its ability to act as a compatibilising agent. Conventional additives such as tackifiers, and antioxidants may be present to modify, adjust and stabilise the adhesive and other properties of the matrix.

Trans-polyoctenamer is a crystalline metathesis polymer of cyclooctene with predominantly trans-isomeric double bonds. It is said to contain a mixture of linear polymer and macrocyclic groups within each polymer chain. The trans-polyoctenamer is exemplified by the materials Vestenamer 6213 and 8012, which are available from Hüls AG. The polymer as available from Hüls AG is said to contain 15% by weight of cyclic oligomers and 85% of acyclic polymer. The crystallinity of the polymer is thermally reversible and reforms very rapidly on cooling the polymer below its melting point. While the inventors do not wish to be bound by any particular theory of action, it is believed that the high ring content in the polymer chains serves to aid compatibility between otherwise incompatible elastomers. Also, the polymer crystallinity and the high ring content increases the amount of network formation within the permanently tacky pressure sensitive adhesive continuous phase. Further, the low content of double bonds in the polymer improves the thermal and oxidative stability of the formulation, while the low viscosity of molten trans-polyoctenamer aids the processing of these materials.

Particularly suitable as bases for the pressure sensitive adhesives of the invention are rubbers such as linear or radial A-B-A block copolymers or mixtures of these A-B-A block copolymers with simple A-B block copolymers. These block copolymers can be based on styrene-butadiene, styrene-isoprene, and hydrogenated styrene-diene copolymers such as styrene ethylene-butylene.

Suitable styrene-diene copolymers for the practice of the invention are exemplified by a-blend of linear styrene/isoprene/styrene triblock copolymer and linear styrene/isoprene diblock copolymer. Such a material is available from Shell Chemical as Kraton D-1161 and has a bound styrene content of about 15% and a diblock content of 17%. A second example is a blend of linear styrene/isoprene/styrene triblock copolymer and linear styrene/isoprene diblock copolymer available from Shell Chemical as Kraton D-1117 and which has a bound styrene content of about 17% and a diblock content of 33%.

An example of a suitable hydrogenated styrene-diene copolymer is a thermoplastic elastomer comprising a blend of clear linear triblock and diblock copolymer based on styrene and ethylene/butylene, with a bound styrene of 14% mass. Such a material is commercially available from shell Chemical Company as Kraton G-1657. Another example is Kraton G-1652 from Shell Chemical Company, which is a thermoplastic elastomer comprised of a clear linear triblock copolymer based on styrene and ethylene-butylene, S-E/B-S, with a bound styrene content of about 30% by weight. Also suitable are polymers in which there is a combination of chemically saturated blocks and chemically unsaturated blocks. For example, a branched copolymer consisting of two polyisoprene chains attached to the rubber midblock of a styrene/ethylene-butylene/styrene triblock copolymer. Such a material is available from Shell Chemical Company as Kraton Resesrch Product RP6919. This material has a styrene content of 18%, and isoprene content of 36% and an ethylene-butylene content of 46% by weight. Also, a low styrene synthetic copolymer of butadiene and styrene, commonly called SBR rubber, can be used as a solid rubber. When formulated into rubber based hot melt pressure sensitive adhesives, the range of trans-polyoctenamer can be up to 36 wt. % of the total formulation.

Also particularly suitable are acrylic pressure sensitive adhesives, exemplified by an acrylic hot melt adhesive manufactured by Schenectedy Chemicals and having the designation Durotac 401. Another example is an acrylic solvent adhesive from Avery Chemicals called Polytex 7600. When formulated into acrylic based pressure sensitive adhesives, the range of trans-polyoctenamer can be up to 60 wt. % of the total formulation.

One aspect of the present invention relates to hot melt pressure sensitive adhesives that are processable at lower temperatures than prior art materials. The rubbery trans-polyoctenamer polymer may be incorporated into the formulations of the instant invention at relatively low temperatures, say at 80–90° C. The thermoplastic elastomers of prior art integrated formulations must be processed at temperatures of at least 160° C., and preferably under a nitrogen atmosphere, in order to melt the thermoplastic elastomer and plasticise it effectively. The trans-polyoctenamer polymer melts at much lower temperatures. At these lower processing temperatures, fewer unwanted side reactions or thermal and oxidative degradation occurs and lower quantities of processing stabilisers can be used.

Other ingredients such as tackifiers, plasticisers, and polymer stabilisers may be added, to modify tack and optimise adhesion properties and to protect polymers from degradation during processing.

Optional fillers such as silica and pigments and optional active ingredients such as, for example, antimicrobial compounds may also be incorporated into the compositions of the invention, Silver sulfadiazine and benzalkonium chloride represent non-limiting examples of such antimicrobial ingredients.

In general, a prior art rubber based pressure sensitive adhesive consists of 20 to 60 wt. % synthetic rubber, 20 to 80 wt. % liquid and/or solid tackifier, 0 to 20 wt. % plasticiser and 0 to 4 wt. % antioxidant and optional other additives. Up to 60 wt. % of the rubber may be replaced by trans-polyoctenamer, which means that up to 36 wt. % of the formulation may be composed of trans-polyoctenamer.

A prior art acrylic based pressure sensitive adhesive will in general be comprised of 50 to 100 wt. % acrylic rubber and 0 to 50 wt. % liquid and/or solid tackifier. Up to 60 wt. % of the acrylic rubber may be replaced by trans-polyoctenamer, which means that up to 60wt. % of the formulation may be trans-polyoctenamer.

The adhesive compositions of the invention may be conveniently prepared as follows. The components of the continuous phase such as polyisobutylene, solid rubber, for example a styrene-olefin-styrene copolymer and any liquid ingredients such as a liquid rubber or a plasticiser are blended together in a suitable mixer, normally a sigma blade or Z-blade mixer with an extruder discharge. If thermoplastic elastomers are used, the mixer will need to be heated to about 170° C. A nitrogen flow of about 60 ml/sec through the mixer reduces the possibility of oxidative degradation of the rubber during processing. About 1% phr of a suitable stabiliser can be added at this stage. After blending of the rubbers, tackifiers, plasticisers etc. the mixer is usually cooled to 90–105° C. and the trans-polyoctenamer, if present, and blended in for a period of time, usually 20–30 min. If high molecular weight rubbers are used, they may need to be premasticated in the mixer or pre-milled on a rubber mill. The fully mixed mass is then removed from the mixer and then coated using conventional techniques on to suitable substrates.

An alternative solvent process can be employed. The acrylic solvent adhesive will be blended in a suitable screw mixer, toluene can be added to ease the salvation.

Typical blending time is between 30 to 180 minutes. Blend can be heated up to 50° C. to aid solution of the trans-polyoctenamer.

Test Methods

The formulations prepared in the examples were evaluated using a number of different test methods. Descriptions of these test methods follow.

Reverse tack

Reverse tack of adhesives is the maximum force necessary to remove a standard polyester strip brought into contact with the adhesive without external force, from this adhesive surface.

Procedure

Make the test panel self adhesive using double coated tape. Laminate the adhesive on the test panel and place the test panel in the lower clamp of a tensile tester. Program the tensile tester. Place a polyester test strip of thickness 125 $\mu$m (5 mils) and dimensions (21 cm×2.54 cm) in the upper clamp, making sure that the total length of polyester under the clamp (loop) is 15 cm. Remove the release liner from the adhesive and start the measurement.

The reverse tack is the maximum force to remove the polyester strip from the adhesive surface.

Peel Adhesion of Adhesive on Stainless Steel or Polyethylene

Peel adhesion is the average force to remove an adhesive, laminated under specified conditions on a stainless steel panel, from the stainless steel panel at constant speed and at a specified angle, usually 90° or 180°.

Procedure

Clean the stainless steel panel with solvent. Use a clean unaged sample of polyethylene. Cut a sample of adhesive 25.4 mm width and reinforce with tape, laminate a paper strip at one end of the sample using an overlap of about 1 cm. Remove the liner from the sample and laminate on the stainless steel panel with a 450 gm. roller at a speed of 150 cm/min. Allow the sample to dwell for 1 minute. Place the paper strip in the upper clamp and the stainless steel panel on the lower clamp, making sure that the angle between peel direction and stainless steel panel is 90°. Start the measurement using a crosshead speed of 300 mm/min. The angle must be kept 90° until the measurement is completed. The 90° peel adhesion is the average force to remove the hydrocolloid strip from the stainless steel panel.

Static Shear of Adhesives

Static shear is the time necessary to remove an adhesive, laminated on a stainless steel panel under specified conditions, from the test panel under influence of a specified weight.

Procedure

Condition the samples at 23±1° and 50±2% relative humidity for 24 hours. Clean the stainless steel shear panel with solvent. Cut a strip of 25.4 mm width and 50 mm length. Reinforce the strip with reinforcing tape. Laminate the strip on the test panel using an overlap surface of 6.45 cm² (1 inch²). Protect the free adhesive with release liner. Put a weight of 500 g on the laminate for 1 hour. Reinforce the free adhesive zone with reinforcing-plastic and perforate. Place the test panel with adhesive on the shear bar using a shear weight of 500 g. Re-zero the registration clock. Note the time on the clock when the measurement is completed.

The invention will now be further described by reference to the following non-limiting examples.

EXAMPLES 1–3

The rubber was added to half the Escorez resin and the two antioxidants in a small Z-blade at 190° C. The mixer was flushed out with nitrogen gas throughout the preparation. The rubber was added, and after a homogeneous melt was achieved, the Vestenamer was added, followed by the remainder of the Escorez resin and all the Adtac LV-E. The mix was allowed to mix thoroughly and was dumped from the mixer into a release coated container. The compositions are shown in Table 1A and the test results in Table 1s.

TABLE 1A

| Component wt % | Example 1 | Example 2 | Example 3 |
| --- | --- | --- | --- |
| Kraton D-1161NS | 37.71 | 22.71 | 17.71 |
| Escorez 2203 LC | 41.68 | 41.68 | 41.68 |
| Adtac LV-E | 19.87 | 19.87 | 19.87 |
| Irganox 565 | 0.25 | 0.25 | 0.25 |
| Irgafos 168 | 0.50 | 0.50 | 0.50 |
| Vestenamer 6213 | — | 15.00 | 20.00 |
| Total | 100.0 | 100.0 | 100.0 |

TABLE 1B

| Test | Example 1 | Example 2 | Example 3 |
| --- | --- | --- | --- |
| Tack N/25 mm | 51.05 | 40.61 | 35.96 |
| 90° Peel on PE | 9.66 | 10.22 | 11.11 |
| 180° Peel on SS | 24.40 | 38.93 | 13.80 |
| Static shear, min |  | 1306 | 233 |

EXAMPLES 4–5

A small Z-blade mixer was purged with nitrogen gas and heated to 160° C. The speed of the front, faster, blade was 30 rpm. The Kraton KD-1161N and the Irganox 1010 were charged to the Mixer at 160° C., and the mixer was started. After mixing for 5 minutes, the rubbery crumb coalesced, and 50 gm of the LVSI-101 was added with continued mixing and nitrogen purging. After a further 10 minutes, the temperature was raised to 170° C. and the mixer front blade speed increased to 47 rpm. The LVSI had at this point completely mixed with the rubber, and a further 51 gm of LVSI was added. 10 minutes later, after blending of the second portion of the LVSI, a further 48 gm of LVSI was added, and mixed for a further 10 minutes. In this way, approximately 50 gm portions of the charge of LVSI were added every 10 minutes until all the 400 gm had been added. 15 minutes later, the adhesive was dumped from the mixer. The total time for this operation was about 90 minutes.

In a similar way, the adhesive of example 5 was prepared, except that the trans-polyoctenamer was added last, after allowing the mixer and its contents to cool to about 90° C., when the trans-polyoctenamer was incorporated within just a few minutes. The compositions are set out in Table 2A and the test results in Table 2B.

TABLE 2A

| Component wt % | Example 4 | Example 5 |
| --- | --- | --- |
| Kraton D-1161NS | 19.84 | 15.87 |
| LVSI-101 | 79.37 | 63.50 |
| Irganox 1010 | 0.79 | 0.63 |
| Vestenamer 6213 | — | 20.0 |
| TOTAL | 100.0 | 100.0 |

TABLE 2B

| Test | Example 4 | Example 5 |
| --- | --- | --- |
| Tack N/25 mm | 11.47 | 9.19 |
| 90° Peel on PE | 3.63 | 2.01 |
| 180° Peel on SS | 5.44 | 4.87 |
| Static Shear, min | 109 | 316 |

EXAMPLES 6 AND 7

In a similar way to the adhesives of Examples 1–3, the examples 6 and 7 were prepared. The compositions are set out in Table 3

TABLE 3

| Component wt. % | Example 6 | Example 7 |
| --- | --- | --- |
| Kraton G-1657 | 30.0 | 15.0 |
| Regalite R91 | 41.0 | 41.0 |

TABLE 3-continued

| Component wt. % | Example 6 | Example 7 |
|---|---|---|
| Regalite R10 | 29.0 | 29.0 |
| Irganox 1010 | 0.3 | 0.3 |
| Vestenamer 6213 | — | 15.0 |
| Total | 100.0 | 100.0 |

EXAMPLES 8 AND 9

The acrylic hot melt adhesive Duratac 401 was blended with trans-polyoctenamer Vestenamer 6213 in a Z-blade mixer to give the compositions set out in Table 4.

TABLE 4

| Component wt. % | Example 8 | Example 9 |
|---|---|---|
| Durotac 401 | 100.0 | 80.0 |
| Vestenamer 6213 | — | 20.0 |
| Total | 100.0 | 100.0 |

EXAMPLE 10

A small glass jar was filled with the Polytex solvent acrylic adhesive, the screw starts to mix at 20 rpm, and the trans-polyoctenamer was added very slowly. After the total amount is added the mix is heated to 50° C. and screw speed is increased to 30 rpm. After mixing for 60 minutes, the adhesive was dumped from the mixer to give the composition shown in Table 5.

TABLE 5

| Component | wt. % |
|---|---|
| Polytex 7600 | 95.0 |
| Vestenamer 6213 | 5.0 |
| Total | 100.0 |

The Polytex 7600 consists of 36 wt % solid polymer and 64 wt % solvent (solvent composition toluene/n-hexane—70/30 wt %). The composition of dry ingredients after evaporation of solvent is shown in Table 6.

TABLE 6

| Component | wt. % |
|---|---|
| Polytex 7600 (dry) | 87.25 |
| Vestenamer 6213 | 12.75 |
| Total | 100.0 |

What is claimed is:

1. A pressure-sensitive hot melt adhesive composition comprising one or more pressure-sensitive adhesive matrices, based on one or more polymers selected from polyisobutylene, butyl rubber, polyacrylates, polyurethanes, silicone gum, natural gum rubber, SBR rubber, polyvinyl ether, styrene-diene block copolymers and blends thereof, and including at least one thermoplastic elastomer, wherein the adhesive composition additionally comprises at least 0.5 weight %, based on the total formulation, of transpolyoctenamer.

2. An adhesive composition according to claim 1 which contains 2 to 60 wt. % of transpolyoctenamer.

3. An adhesive composition according to claim 2 which contains 5 to 40 wt. % of transpolyoctenamer.

4. An adhesive composition according to claim 3 which contains 10 to 30 wt. % of transpolyoctenamer.

5. An adhesive composition according to any one of the preceding claims which additionally contains a tackifier and/or a plasticizer.

6. An adhesive composition according to claim 1 wherein the one or more adhesive matrices is or are based on a styrene-butadiene or styrene-isoprene block copolymer.

7. An adhesive composition according to claim 1 which comprises the following components in the following percentages by weight:

| Synthetic rubber: | 8–59.5% |
|---|---|
| transpolyoctenamer: | 0.5–36% |
| Tackifier: | 20–80% |
| plasticizer: | 0–20% |
| Antioxidant: | 0–4% | wherein the weight ratio of transpolyoctenamer, to synthetic rubber does not exceed 3:2.

8. An adhesive composition according to claim 1 which comprises the following components in the following percentages by weight

| Acrylic rubber | 30–99.5% |
|---|---|
| Transpolyoctenamer | 0.5–60% |
| Tackifier | 0–50% | wherein the weight ratio of transpolyoctenamer to acrylic rubber does not exceed 3:2.

9. A method of making a pressure-sensitive hot melt adhesive composition which comprises blending transpolyoctenamer into a pressure-sensitive adhesive matrix material, in an amount of at least 0.5 wt. % based on the total composition, at a temperature not exceeding 105° C.

* * * * *